US010352850B2

(12) United States Patent
Ochi et al.

(10) Patent No.: US 10,352,850 B2
(45) Date of Patent: Jul. 16, 2019

(54) CALORIE MEASUREMENT DEVICE

(71) Applicant: Panasonic Intellectual Property Management Co., Ltd., Osaka (JP)

(72) Inventors: Kazuhiro Ochi, Kyoto (JP); Tatsuya Takahashi, Shiga (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 82 days.

(21) Appl. No.: 15/102,769

(22) PCT Filed: Dec. 2, 2014

(86) PCT No.: PCT/JP2014/006029
§ 371 (c)(1),
(2) Date: Jun. 8, 2016

(87) PCT Pub. No.: WO2015/092994
PCT Pub. Date: Jun. 25, 2015

(65) Prior Publication Data
US 2016/0313241 A1    Oct. 27, 2016

(30) Foreign Application Priority Data
Dec. 18, 2013  (JP) .................................. 2013-261689

(51) Int. Cl.
*G01N 33/02* (2006.01)
*G01N 21/359* (2014.01)

(52) U.S. Cl.
CPC ........... *G01N 21/359* (2013.01); *G01N 33/02* (2013.01); *G01N 2201/068* (2013.01);
(Continued)

(58) Field of Classification Search
CPC ................. G01N 21/359; G01N 33/02; G01N 2201/068; G01N 2201/121; G01N 2201/1211; G01N 2201/1214
See application file for complete search history.

(56) References Cited

U.S. PATENT DOCUMENTS

2007/0218174 A1   9/2007  Hanamatsu et al.
2012/0053426 A1*  3/2012  Webster ................. G01N 22/04
                                                        600/301
(Continued)

FOREIGN PATENT DOCUMENTS

JP    2004-184172 A    7/2004
JP    2005-017210 A    1/2005
(Continued)

OTHER PUBLICATIONS

International Preliminary Report on Patentability issued in Application No. PCT/JP2014/006029 dated Jun. 21, 2016.
(Continued)

*Primary Examiner* — Christine S. Kim
(74) *Attorney, Agent, or Firm* — McDermott Will & Emery LLP

(57) ABSTRACT

This calorie measurement device is provided with the following: a light-emission unit that exposes a food article to light that contains near-infrared wavelengths; a light-reception unit that receives transmitted light that had passed through the food article and/or reflected light that was reflected by the food article; a correction unit that computes a base absorbance for the food article on the basis of the transmitted and/or reflected light and corrects the light intensity measured by the light-reception unit and/or the computed base absorbance on the basis of affecting factors, said affecting factors being those that affect the absorption and reflection of light by the food article but are essentially unaffected by the light-absorption and light-reflection properties of the components of the food article; and an analysis unit that computes an analysis value indicating the caloric content of the food article on the basis of the corrected light intensity measured by the light-reception unit and/or the corrected base absorbance.

5 Claims, 5 Drawing Sheets

10: Calorie Measurement Device
20: Measurement Unit
22: Light Emitter
24: Light Receiver
30: Analyzer

(52) U.S. Cl.
CPC .............. *G01N 2201/121* (2013.01); *G01N 2201/1211* (2013.01); *G01N 2201/1214* (2013.01)

(56) References Cited

U.S. PATENT DOCUMENTS

| | | | | |
|---|---|---|---|---|
| 2014/0185046 | A1* | 7/2014 | Urushidani | G01N 21/359 356/402 |
| 2014/0240508 | A1* | 8/2014 | Gomi | G01J 3/2823 348/162 |
| 2015/0138538 | A1* | 5/2015 | Sakurai | G01J 3/0291 356/72 |
| 2015/0204832 | A1* | 7/2015 | Ochi | G01N 21/3554 702/30 |
| 2015/0253254 | A1* | 9/2015 | Takahashi | G01N 33/02 356/300 |
| 2015/0281535 | A1* | 10/2015 | Korenaga | G01N 33/025 348/360 |
| 2016/0091369 | A1* | 3/2016 | Sakurai | G01J 3/26 356/402 |
| 2016/0140870 | A1* | 5/2016 | Connor | G09B 19/0092 356/51 |

FOREIGN PATENT DOCUMENTS

| | | |
|---|---|---|
| JP | 2005-292128 A | 10/2005 |
| JP | 2008-122412 A | 5/2008 |
| JP | 2008-203234 A | 9/2008 |
| WO | WO 2006046197 A1 * | 5/2006 ......... G01G 19/4146 |

OTHER PUBLICATIONS

International Search Report issued in Application No. PCT/JP2014/006029 dated Mar. 3, 2015, with English translation.

* cited by examiner

10: Calorie Measurement Device
20: Measurement Unit
22: Light Emitter
24: Light Receiver
30: Analyzer

US 10,352,850 B2

CALORIE MEASUREMENT DEVICE

RELATED APPLICATIONS

This application is the U.S. National Phase under 35 U.S.C. § 371 of International Application No. PCT/JP2014/006029, filed on Dec. 2, 2014, which in turn claims the benefit of Japanese Application No. 2013-261689, filed on Dec. 18, 2013, the disclosures of which are incorporated by reference herein.

TECHNICAL FIELD

The present invention relates to a calorie measurement device that measures calories of food.

BACKGROUND ART

A conventional calorie measurement method calculates calories of food based on the amount of protein, fat, and carbohydrate per unit, weight of a food and an energy conversion factor corresponding to each component. A known method calculates the amount of protein based on, for example, the amount of nitrogen quantitated with a Kjeldahl method and the conversion factor of nitrogen-protein. Known methods for calculating the amount of fat include, for example, a Soxhlet extraction method, an improved chloroform-methanol extraction method, a Rose-Gottlieb method, or an acid decomposition method. A known method calculates the amount of carbohydrate with a subtraction method. The conventional calorie measurement method requires many processes to calculate calories and is thus complicated.

Patent Document 1 discloses a calorie measurement device that includes a plate on which food is arranged, a light emitter that irradiates a food with near-infrared light, a light receiver that receives the light reflected by the food, an operation button that starts calorie measurement, and the like. The measurement device calculates the absorbance of the food based on the light received by the light receiver and calculates the calories of the food based on the calculated absorbance.

Such a measurement device allows a user to know the calories of the food just by arranging the food subject to measurement on a plate and operating an operation button to perform measurement. This reduces the burden on the user as compared to the conventional calorie measurement method.

PRIOR ART DOCUMENT

Patent Document

Patent Document 1: Japanese Laid-Open Patent Publication No. 2008-122412

SUMMARY OF THE INVENTION

Problems That Are to be Solved by the Invention

The amount of light received by the light receiver of Patent Document 1 is affected by various factors such as an optical path in a food, the reflectance of the food, and the ambient temperature. However, the calorie measurement device of Patent Document 1 calculates calories without taking into account the influence of such factors. Thus, the calculated calories may greatly differ from the actual food calories.

It is an object of the present invention to provide a calorie measurement device that contributes to increasing the measurement accuracy of food calories.

Means for Solving the Problem

One aspect of the present invention is a calorie measurement device that analyzes a food for calories. The calorie measurement device includes a light emitter, a light receiver, a correction unit, and an analyzer. The light emitter irradiates the food with light having a near-infrared wavelength. The light receiver receives at least one of transmitted light that has been transmitted through the food and reflected light that has been reflected by the food. The correction unit calculates a basic absorbance of the food based on at least one of the transmitted light and the reflected light and corrects at least one of the calculated basic absorbance and a light reception amount received by the light receiver based on an influential factor. The influential factor affects absorption and reflection of light by a food and is not substantially affected by characteristics of the absorption and the reflection of the light of a food component. The analyzer calculates an analyzed value indicating the calorie of the food based on at least one of the corrected basic absorbance and the corrected light reception amount received by the light receiver.

In the above structure, it is preferred that the correction unit specify a degree of influence the influential factor has on the absorption and the reflection of the light in a food based on an absorbance in a predetermined wavelength range of the transmitted light or the reflected light that is not substantially affected by the characteristics of the absorption and the reflection of the light of the food component and correct at least one of the calculated basic absorbance and the light reception amount received by the light receiver in accordance with the specified degree of the influence.

In the above structure, it is preferred that the correction unit correct at least one of the calculated basic absorbance and the light reception amount received by the receiver based on the influential factor that reflects a light path in a food.

In the above structure, it is preferred that the correction unit correct at least one of the calculated basic absorbance and the light reception amount received by the receiver based on the influential factor that reflects at least one of a reflectance and a transmittance of a food.

In the above structure, it is preferred that the correction unit correct at least one of the calculated basic absorbance and the light reception amount received by the receiver based on an environmental factor that is the influential factor that affects a wavelength of a peak of the absorbance of a food.

In the above structure, it is preferred that the correction unit correct at least one of the calculated basic absorbance and the light reception amount received by the receiver based on a color of a food that is the influential factor.

Effect of the Invention

The present calorie measurement device contributes to accurate calculation of food calories.

EMBODIMENTS OF THE INVENTION

First Embodiment

Figure 1:
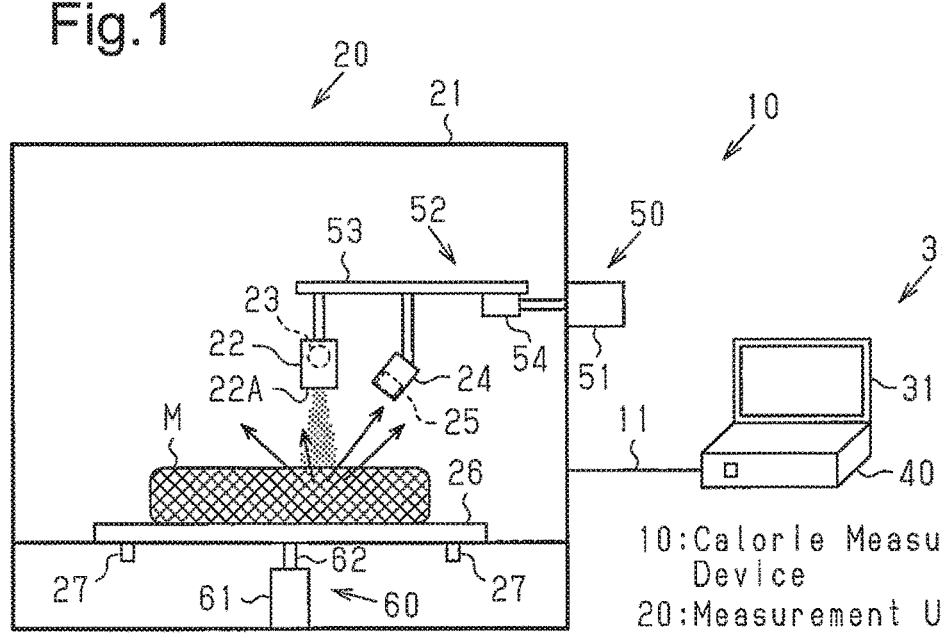
FIG. 1 is a schematic diagram showing a first embodiment of a calorie measurement device.

The schematic structure of a first embodiment of a calorie measurement device 10 will now be described with reference to FIG. 1.

The calorie measurement device 10 includes a measurement unit 20 and an analyzer 30. The measurement unit 20 and the analyzer 30 are connected to each other by a connection cable 11.

The measurement unit 20 includes a housing 21. The measurement unit 20 includes a light emitter 22, a light receiver 24, a table 26, weight detectors 27, a table drive unit 60, and a measurement drive unit 50, which are arranged in the housing 21. The measurement unit housing 21 includes a door (not shown). The inner side of the measurement unit housing 21 is shielded from light by closing the door.

The light emitter 22 includes a light source 23. The light emitter 22 is arranged above a food M on the table 26. The light source 23 emits light having at least a wavelength of a near-infrared region. The light source 23 includes, for example, a halogen lamp. The light emitter 22 may be tubular, and the inner circumferential surface of the light emitter 22 may be formed to be mirror-like. Thus, the light emitter 22 guides light from the light source 23 to an opening 22A.

The light receiver 24 includes an optical filter 25. The light receiver 24 is located at a position where the light receiver 24 can receive the light reflected from the food M. The light receiver 24 is formed by, for example, a silicon element. From the light reflected from the food M, the optical filter 25 selectively transmits light having a wavelength in a particular region of the near-infrared region. Further, the optical filter 25 is configured to be capable of changing the transmitted wavelength in accordance with a control signal from the analyzer 30. The light receiver 24 generates a light reception amount signal that changes in accordance with the amount of received light that has been transmitted through the optical filter 25.

The table 26 includes a circular flat surface. The food M, which is the measured subject, is arranged on the surface of the table 25 that opposes the light emitter 22 and the light receiver 24.

The weight detectors 27 are located at the lower side of the table 26 to detect the weight of the table 26 and the food M. The weight detectors 27 provide the analyzer 30 with information indicating the weight of the food M in which the weight of the table 26 is subtracted from the detected weight.

The measurement drive unit 50 includes a movement motor 51 and a sliding mechanism 52. The sliding mechanism 52 includes a rack 53 and a pinion 54. The measurement drive unit 50 is located above the table 26 and extends in the radial direction of the table 26. The light emitter 22 and the light receiver 24 are suspended from the rack 53. The pinion 54 is connected to the movement motor 51 and engaged with the teeth of the rack 53.

When the movement motor 51 is driven to rotate the pinion 54, the rack 53 moves in the radial direction of the table 26 above the table 25. Thus, when the rack 53 moves, the light emitter 22 and the light receiver 24 move in the radial direction of the table 26 above the table 26.

The table drive unit. 60 supports the table 26 from below. The table drive unit 60 includes a rotation motor 61 and a rotation shaft 62 that connects the center of the table 26 to the rotation motor 61. When the rotation motor 61 is driven, the table 26 rotates around the center of the table 26 (hereinafter referred to as "circumferential direction").

Figure 2:
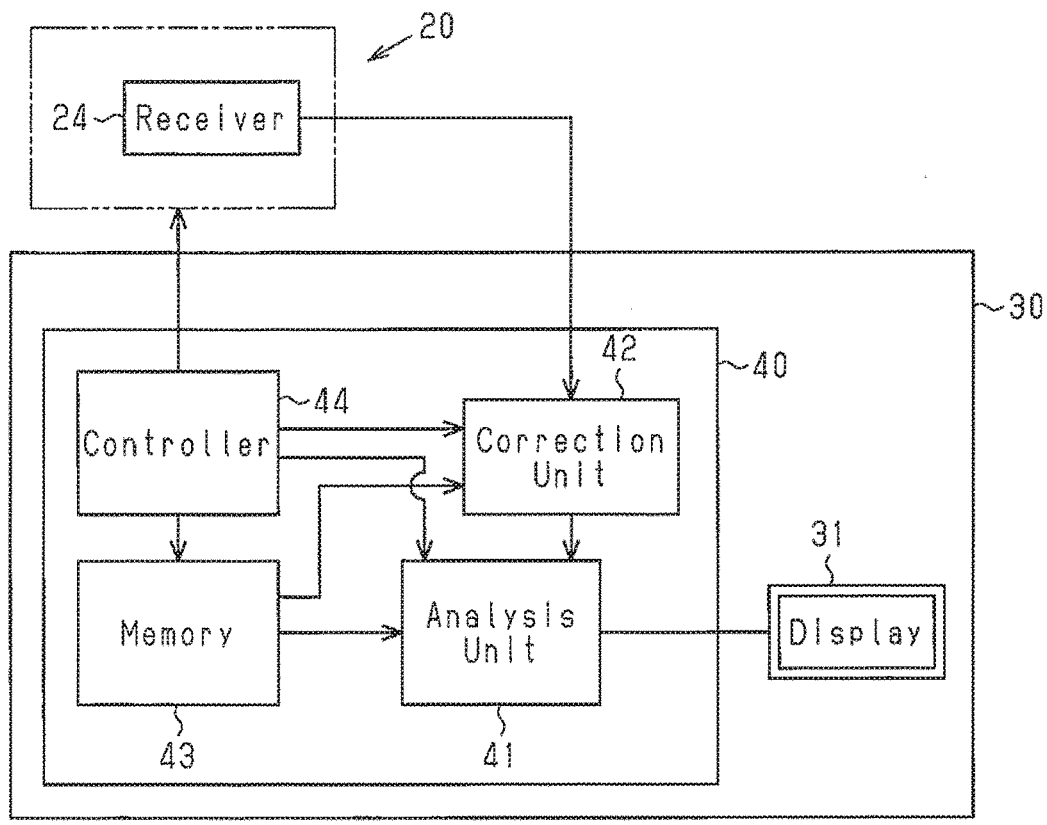
FIG. 2 is a block diagram showing an analyzer of the first embodiment.

The configuration of the analyzer 30 will now be described with reference to FIG. 2.

The analyzer 30 includes an analyzer housing 40. The analyzer 30 includes an analysis unit 41, a correction unit 42, a memory 43, and a controller 44, which are arranged in the analyzer housing 40. Further, the analyzer 30 includes a display 31.

The memory 43 stores a regression equation obtained from the multiple regression analysis of a secondary differential spectrum in the absorbance of the light, received by the light receiver 24. The regression equation estimates food calories, which serve as dependent variables, using the absorbance of each wavelength of the light received by the light receiver 24, which serves as an independent variable, and the contribution coefficient of the absorbance of each wavelength. Further, the memory 43 stores a reference absorbance that is used when the correction unit 42 performs correction.

The correction unit 42 receives the light reception amount signal from the light receiver 24 of FIG. 1. The correction unit 42 functions to calculate the absorbance of the food M from the light reception amount signal. The absorbance is calculated by obtaining a common logarithm that has a proportion of the amount of light received by the light receiver 24 relative to the amount of light that the light emitter 22 irradiates the food M with. Further, the correction unit 42 functions to change the calculated absorbance using the reference absorbance, which is stored in the memory 43.

The analysis unit 41 functions to estimate the calories of the food M arranged on the measurement unit 20 by applying the absorbance output by the correction unit 42 to the regression equation stored in the memory 43. The display 31 shows the information that is output from the analysis unit 41.

The controller 44 outputs a control signal that controls the operation of each block in the measurement unit 20 and the analyzer 30.

The operation for measuring the calories of the food M using the calorie measurement device 10 of FIGS. 1 and 2 will now be described.

First, the calorie measurement operation when the correction unit 42 does not perform absorbance correction will now be described.

The light emitter 22 irradiates the food M on the table 26 with the light emitted through the opening 22A from the light source 23. The light from the light emitter 22 irradiating the food M is partially absorbed in accordance with the characteristics of the absorption and reflection of the light of components of the food M. Further, the light emitted from the light emitter 22 to the food M is partially reflected by the food M.

The light receiver 24 receives the reflected light of the near-infrared region that is reflected from the food M and transmitted through the optical filter 25. In such a case, the analyzer 30 controls the optical filter 25 to sequentially switch the wavelength of the light reflected from the food M and transmitted through the optical filter 25. The light receiver 24 outputs, to the correction unit 42, the light reception amount signal in accordance with the amount of received light having the wavelength sequentially switched by the optical filter 25 and transmitted through the optical filter 25.

The correction unit 42 calculates the absorbance of the food M (uncorrected absorbance will hereinafter be referred to as the basic absorbance) from the light reception amount signal of the light receiver 24 and outputs the basic absorbance to the analysis unit 41. In this case, the correction unit 42 calculates the basic absorbance for each wavelength of the near-infrared light that is sequentially transmitted through the optical filter 25 and outputs the calculated basic absorbance to the analysis unit 41.

The analysis unit 41 calculates the calorie per unit weight of the food M by applying the basic absorbance of the food M output by the correction unit 42 to the regression equation stored in the memory 43. The analysis unit 41 calculates the calories of the food M based on the calculated calorie per unit weight of the food M and the weight of the food M output by the weight detector of FIG. 1.

To increase the measurement points of the food M and improve the measurement accuracy, the calorie measurement device 10 controls the measurement drive unit 50 of FIG. 1 to move the light emitter 22 and the light receiver 24 in the radial direction of the table 26. Thus, the light emitter 22 emits the light from the light source 23 to a different position in the radial direction of the table 26 of the food M. Further, the calorie measurement device 10 controls the table drive unit 60 to rotate the food M on the table 26 in the circumferential direction. This allows the light, emitter 22 to emit the light from the light source 23 to a different position in the circumferential direction of the food M.

The calorie measurement device 10 emits the light from the light emitter 22 to different positions on the food M to perform the calorie measurement operation and measure calories using a number of locations on the food M. The calorie measurement device 10 obtains the average value of the calorie measurement results to increase the calorie measurement accuracy of the food M.

As described above, the calorie measurement device 10 calculates the calories of the food M by applying the basic absorbance of light received by the light receiver 24 to the regression equation.

However, the amount of light received by the light receiver 24 when measuring the calories of the food M is changed by the influence of influential factors. The influential factors affect the absorption and reflection of light in the food and are not substantially affected by the characteristics of the absorption and reflection of the light of food components. Examples of the influential factors include the light path, the reflectance of food, and the ambient temperature.

Thus, even when measuring the same food M, the calories of the food M measured by the calorie measurement device 10 are affected and changed by the influential factors. Accordingly, the calorie measurement device 10 is affected by the influential factors. This decreases the calorie measurement accuracy of the food M.

The operation for limiting decreases in the calorie measurement accuracy of the food M in the calorie measurement device 10 that is affected by the influential factors will now be described.

Figure 3:
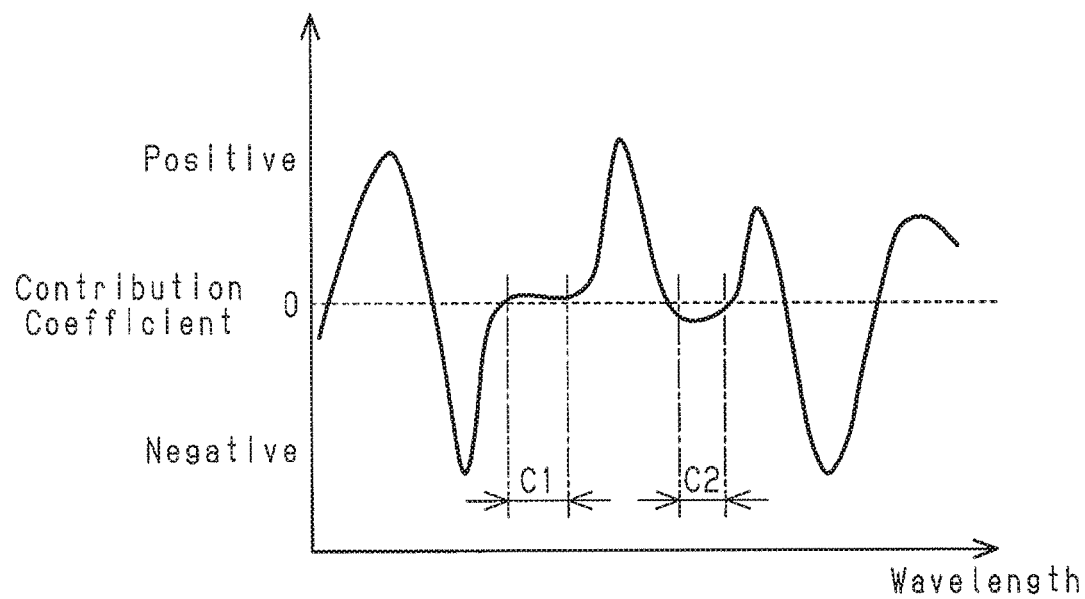
FIG. 3 is a graph showing the wavelength and the contribution coefficient in the first embodiment.

FIG. 3 shows the contribution coefficient relative to the wavelength of light received by the light receiver 24 in the regression equation that is obtained through the multiple regression analysis. The contribution coefficient has peaks in multiple wavelength regions. The wavelength region of the peak of the contribution coefficient has a strong correlation with the wavelengths of the peaks of the basic absorbances of protein, fat, and carbohydrate of the food M.

In FIG. 3, the contribution coefficient corresponding to the components of food such as water that has a peak in the basic absorbance and makes a subtle contribution to the calories is indicated as a negative value.

As shown by a first wavelength region C1 and a second wavelength region C2, the contribution coefficient of the regression equation includes a wavelength region having an extremely small value. The first wavelength region C1 and the second wavelength region C2 of the light irradiating the food M are not substantially affected by the characteristics of the absorption and reflection of the light of the components of the food M.

The calorie measurement device 10 specifies the degree of influence of the influential factors based on the difference between the reference absorbance stored in the memory 43 and the basic absorbances of the first wavelength region C1 and the second wavelength region C2 in the light received by the light receiver 24. The calorie measurement device 10 corrects the basic absorbance calculated from the light reception amount signal of the light receiver 24 based on the specified degree of influence. The reference absorbance stored in the memory 43 is the basic absorbance of the first wavelength region C1 and the second wavelength region C2 of light received by the light receiver 24 when measuring a large variety of calorie-known sample foods with the calorie measurement device 10 to obtain the regression equation.

That is, the memory 43 stores the reference absorbance corresponding to the influential factors. The correction unit 42 reads the reference absorbance from the memory 43, calculates the amount of correction from the difference of the calculated basic absorbance and the reference absorbance, and corrects at least one of the basic absorbance and the amount of light received by the light receiver in accordance with the calculated amount of correction. For example, the reference absorbance corresponding to the influential factors includes the reference absorbance of a predetermined wavelength range of transmitted light or reflected light that is not substantially affected by the characteristics of the absorption and reflection of the light of food components. In this case, the correction unit 42 calculates the amount of correction from the difference of the reference absorbance and the basic absorbance calculated in the predetermined wavelength range of the transmitted light or the reflected light. For example, the food components include at least one of protein, fat, and carbohydrate.

The analysis unit 41 calculates the calories of the food N using the corrected basic absorbance. The calorie measurement device 10 calculates the calories by correcting changes in the characteristics of the absorption and reflection of the light in the food M that are affected by the influential factors.

The basic absorbance that is in accordance with the amount of light received by the light receiver 24 when correction is performed with a fixed amount will now be described with reference to FIG. 4.

Figure 4:
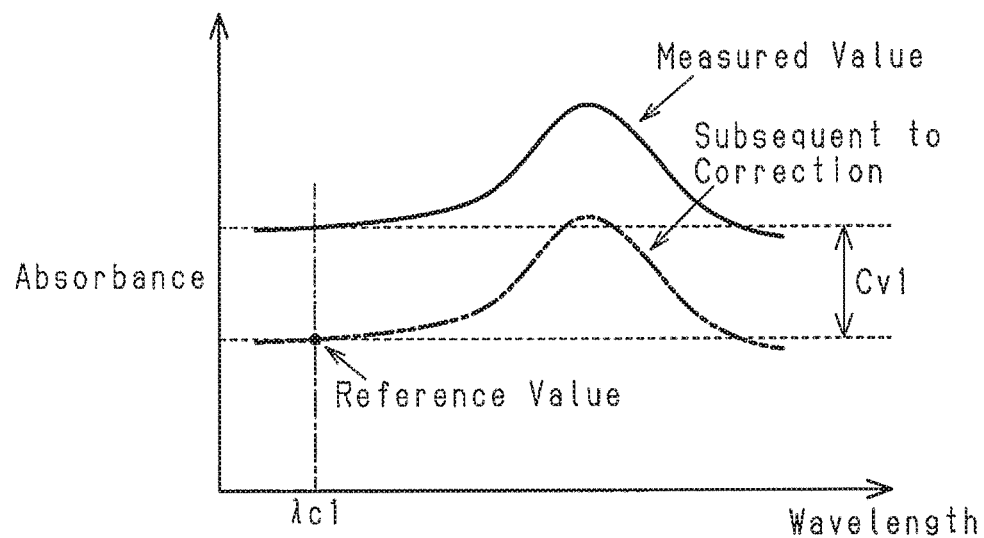
FIG. 4 is a graph showing the wavelength and the absorbance in the first embodiment.

The solid line in FIG. 4 shows the spectrum of the basic absorbance of the amount of light received by the light receiver 24. The broken line in FIG. 4 shows the spectrum of the corrected basic absorbance output from the correction unit 42.

The correction unit 42 performs correction using the basic absorbance of a first correction wavelength $\lambda c1$ of the first wavelength region C1 shown in FIG. 3.

The correction unit 42 calculates a first correction amount Cv1, which is the difference of the reference absorbance and the basic absorbance of the first correction wavelength $\lambda c1$ of light received by the receiver 24. The correction unit 42 uses the first correction amount Cv1 to correct the basic absorbance of light received by the light receiver 24 over the entire wavelength region.

Thus, the correction unit 42 shifts the basic absorbance of a measured value over the entire wavelength region so that the basic absorbance of the first correction wavelength $\lambda c1$ of light received by the light receiver 24 conforms to the reference absorbance.

This allows the calorie measurement device 10 to correct the basic absorbance of light received by the light receiver 24 when measuring the calories of the food M so that the corrected basic absorbance approaches the basic absorbance (reference absorbance) of the light received by the light receiver 24 when measuring many a large variety of sample foods to obtain the regression equation.

The basic absorbance calculated from the amount of light, received by the light receiver 24 that is corrected by linearly approximating the difference of the reference absorbance between two wavelengths having an interval will now be described with reference to FIG. 5.

Figure 5:
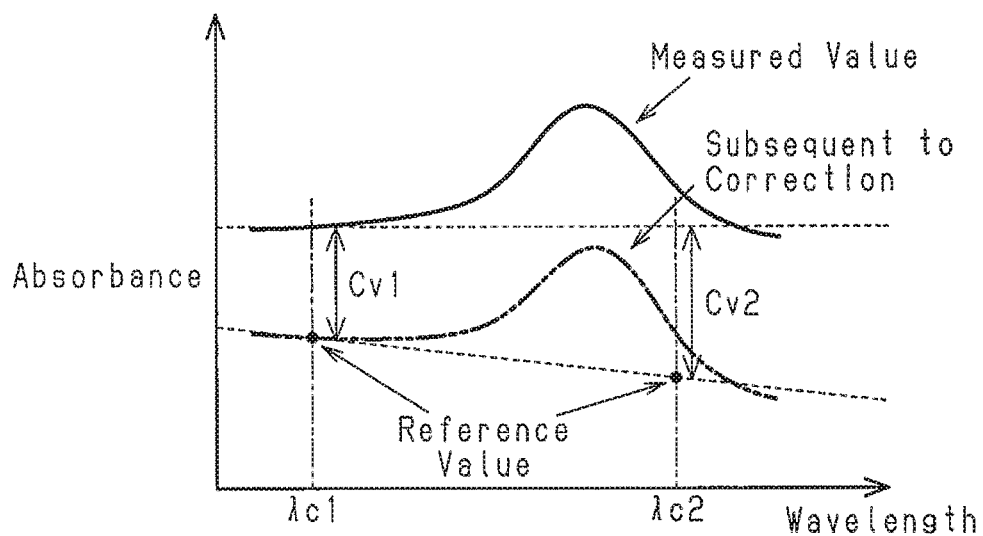
FIG. 5 is a graph showing the wavelength and the absorbance in the first embodiment.

The solid line in FIG. 5 shows the spectrum of the basic absorbance of the amount of light received by the light receiver 24. The broken line in rig. 5 shows the spectrum of the corrected basic absorbance that is output by the correction unit 42.

The correction unit 42 performs correction using the basic absorbance of the first correction wavelength $\lambda c1$ of the first wavelength region C1 and the second correction wavelength $\lambda c2$ of the second wavelength region C2, which are shown in FIG. 3.

The correction unit 42 obtains the first correction amount Cv1, which is the difference of the basic absorbance and the reference absorbance of the first correction wavelength $\lambda c1$, and the second correction amount Cv2, which is the difference of the basic absorbance and the reference absorbance of the second correction wavelength $\lambda c2$, in the light received by the light receiver 24. The correction unit 42 corrects the basic absorbance of the light received by the light receiver 24 over the entire wavelength region with the amount of correction of the value that is obtained by linearly approximating the first correction amount Cv1 and the second correction amount Cv2.

This allows the calorie measurement device 10 to correct the basic absorbance of the light received by the light receiver 24 when measuring the calories of the food M so that the corrected basic absorbance accurately approaches the basic absorbance (reference absorbance) used for measurement that obtains the regression equation.

The basic absorbance calculated from the amount of light received the light receiver 24 that is corrected by curvilinearly approximating the difference of the reference absorbance between three wavelengths having an interval will now be described with reference to FIG. 6.

Figure 6:
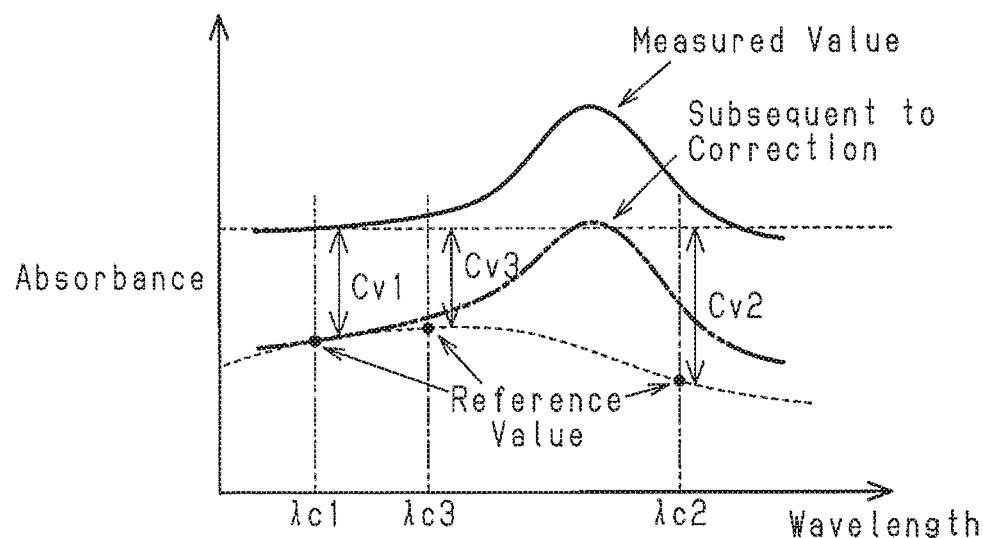
FIG. 6 is a graph showing the wavelength and the absorbance in the first embodiment.

The solid line in FIG. 6 shows the spectrum of the basic absorbance of the amount of light received by the light receiver 24. The broken line in FIG. 6 shows the spectrum of the corrected basic absorbance that is generated by the correction unit 42.

The correction unit 42 performs correction using the basic absorbances of the first correction wavelength $\lambda c1$ and a third correction wavelength $\lambda c3$ of the first wavelength region C1, which is shown in FIG. 3, and the basic absorbance of the second correction wavelength $\lambda c2$ of the second wavelength region C2, which is shown in FIG. 3.

The correction unit 42 obtains the difference of the reference absorbance and the basic absorbances of the first correction wavelength $\lambda c1$, the third correction wavelength $\lambda c3$, and the second correction wavelength $\lambda c2$ as the first correction amount Cv1, a third correction amount Cv3, and the second correction amount Cv2, respectively. The correction unit 42 corrects the basic absorbance of the light received by the light receiver 24 over the entire wavelength region with the amount of correction of the value that is obtained by curvilinearly approximating the first correction amount Cv1, the third correction amount Cv3, and the second correction amount Cv2.

More specifically, the predetermined wavelength range is one of wavelength ranges, and the reference absorbance corresponding to the influential factors includes reference absorbances respectively corresponding to the wavelength ranges. The correction unit 42 calculates correction amounts from the difference between the calculated, basic absorbance and the reference absorbance in the wavelength ranges and corrects at least one of the amount of the light received by the light receiver and the basic absorbance based on the calculated correction amounts. The correction unit 42 calculates the correction amount of the entire wavelength range by linearly or curvilinearly approximating the correction amounts and corrects at least one of the amount of the light received by the light receiver and the basic absorbance in accordance with the calculated correction amount of the entire wavelength range.

This allows the calorie measurement device 10 to correct the basic absorbance of the light received by the light receiver 24 when measuring the calories of the food M so that the corrected basic absorbance further accurately approaches the basic absorbance (reference absorbance) used for measurement that obtains the regression equation.

The calorie measurement device 10 may perform the same operation using the discrete value of a wavelength of the basic absorbance instead of the correction of the basic absorbance with consecutive spectrums of the basic absorbance of the light received by the light receiver 24 of FIGS. 4 to 6.

The calorie measurement device 10 of the present embodiment has the advantages described below.

(1) The calorie measurement device 10 corrects the basic absorbance based on the absorbance of a wavelength that is not substantially affected by the characteristics of absorption and reflection of the light of the components of the food M. Thus, the calorie measurement device 10 reduces the influence of the influential factors of the basic absorbance. Accordingly, the calorie measurement device 10 calculates an analyzed value of the food calorie based on the basic absorbance corrected by the correction unit. This increases the measurement accuracy of the food calories.

(2) The calorie measurement device 10 corrects the basic absorbance of the light received by the light receiver 24 when measuring the calories of the food M based on the difference of the reference absorbance and the basic absorbance of the wavelength of a wavelength region having an extremely small contribution coefficient to the calories of the food M. The light of the wavelength region having an extremely small contribution coefficient is not substantially affected by the influence of changes in the calories of the food M. Thus, the basic absorbance of the wavelength region having an extremely small contribution coefficient shows the absorbance that is changed by the influence of the influential factors other than the calories of the food M. Accordingly, the calorie measurement device 10 reflects the degree of the influence of the influential factors and corrects the basic absorbance. This further increases the measurement accuracy of the food calories.

(3) The calorie measurement device 10 corrects the basic absorbance based on the influence of the influential factors including a light path in the food M. Thus, the calorie measurement device 10 reflects the degree of the influence of the influential factors that reflect the light path in the food M and corrects the basic absorbance. This increases the measurement accuracy of the calorie of the same kind of food M having a different inner light path.

(4) The calorie measurement device 10 corrects the basic absorbance based on the influence of the influential factors including a reflectance of the food. M. Thus, the calorie measurement device 10 reflects the degree of the influence of the influential factors that reflect the reflectance of the food M and corrects the basic absorbance. This increases the measurement accuracy of the calories of the food M that differs in light reflectance resulting from, for example, difference in surface roughness.

Second Embodiment

The calorie measurement device 10 of a second embodiment differs from the calorie measurement device 10 of the first embodiment in the following points in the second embodiment, like or same reference numerals are given to those components that are the same as the corresponding components of the first embodiment. Such components will not be described in detail.

The correction unit 42 of the first embodiment corrects changes in the basic absorbance of the light received by the light receiver 24 that are caused by the influence of the influential factors. The correction unit 42 of the second embodiment corrects changes in the absorbance of the light received by the light receiver 24 that are caused by the influence of the influential factors and changes in the absorbance in accordance with the amount of light received by the light receiver 24 based on the color of the food M.

The amount of light in an infrared light region received by the light receiver 24 changes in accordance with the color of the food M when viewed by emitting light having a wavelength in the visible light region.

Figure 7:
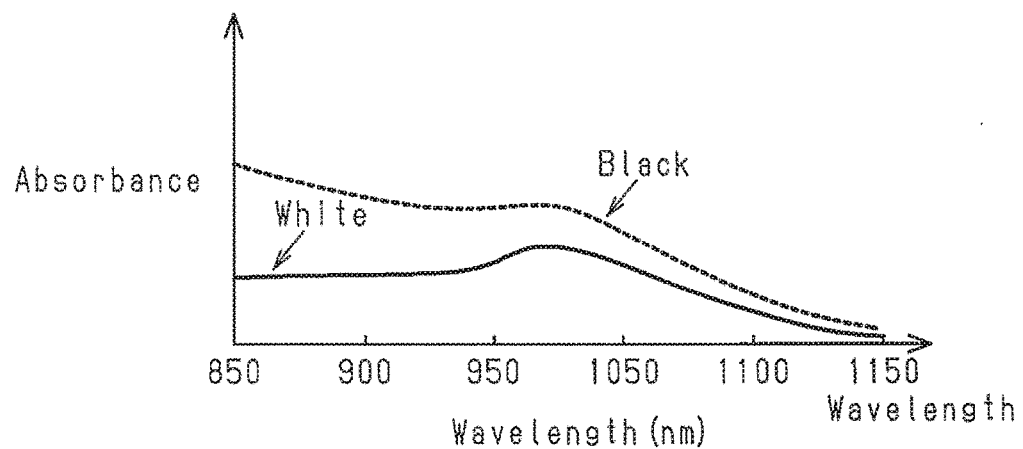
FIG. 7 is a graph showing the wavelength and the absorbance in a second embodiment.

FIG. 7 shows spectrums of the basic absorbances of foods M that have the same calorie and differ in color. The solid line shows the basic absorbance of a white food M. The dotted line shows the basic absorbance of a black food M.

The difference in basic absorbance between the white food M and the black food M having the same calorie increases as the wavelength approaches the visible light region (400 nm to 800 nm). Thus, the calorie calculated by the calorie measurement device 10 in accordance with the color of the food M changes even in the foods M having the same calorie.

The operation of the calorie measurement device 10 for limiting changes in the calorie measured in accordance with the color of the food M will now be described.

An image capturing camera (not shown) is arranged in the measurement unit housing 21 of FIG. 1. The image capturing camera is coupled to where the image capturing camera can capture images of the food M on the table 26.

The calorie measurement device 10 captures images of the food M on the table 26 using the image capturing camera and then outputs the captured image data to the correction unit 42 of the analyzer 30.

The correction unit 42 determines the color of a food based on the image data captured by the image capturing camera. The correction unit 42 corrects the basic absorbance of light received by the light receiver 24 based on the reference absorbance and the determined food color information.

The correction of the basic absorbance of the food M having different colors will now be described with reference to FIG. 8.

Figures 8A, 8B:
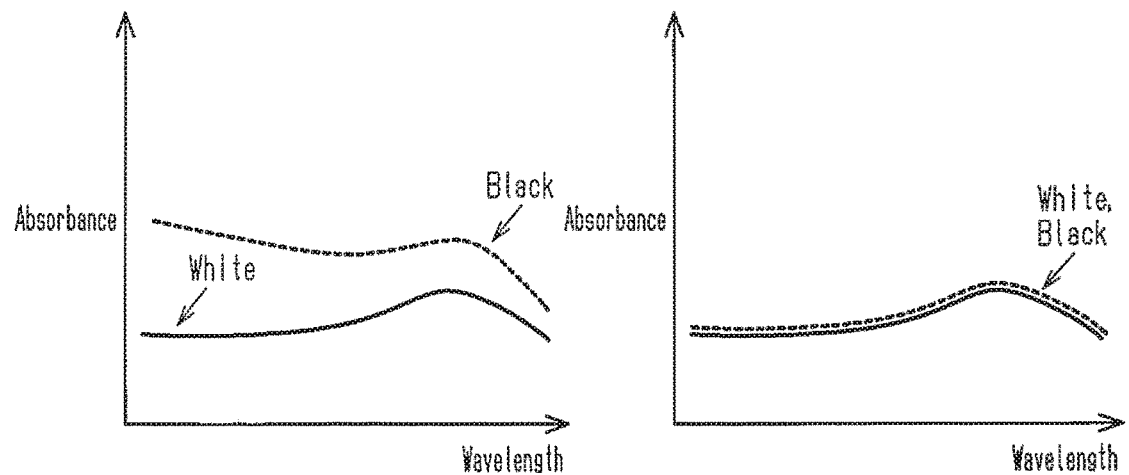
FIG. 8A is a graph showing the wavelength and the absorbance prior to correction in the second embodiment.
FIG. 8B is a graph showing the wavelength and the absorbance subsequent to correction in the second embodiment.

FIG. 8A shows an example of spectrums of the basic absorbances of two foods M that differ in color.

To obtain the regression equation, the calorie measurement device 10 uses a white sample food when measuring a large variety of calorie-known sample foods. Thus, the memory 43 stores, as the reference absorbance, the basic absorbance when the white sample food is measured. Further, the calorie measurement device 10 stores, in the memory 43, the color correction information of statistically obtained correction amounts for the difference of the basic absorbances of other colors of the foods M that are not limited to black from the basic absorbance of the white sample food.

When the food M captured by the image capturing camera is not white, the calorie measurement device 10 corrects the basic absorbance of light received by the light receiver 24 using the color correction information and the reference absorbance that is obtained by measuring the white sample food.

Thus, as shown in FIG. 8E, the basic absorbance of the light received by the light receiver 24 when measuring the black food N is corrected so that the corrected basic absorbance approaches the basic absorbance of the light received by the light receiver 24 when measuring the white food M.

That is, the reference absorbance corresponding to the influential factors includes the basic absorbance of a food having a reference color. The correction unit 42 calculates the amount of correction from the difference of the calculated basic absorbance and the basic absorbance of the food having the reference color. The reference color includes, for example, white.

The calorie measurement device 10 may perform the same operation using the discrete value of a wavelength of the basic absorbance instead of the correction of the basic absorbance with consecutive spectrums of the basic absorbance of the light received by the light receiver 24 of FIGS. 7 and 8.

In addition to advantages (1) to (4) of the calorie measurement device 10 of the first embodiment, the calorie measurement device 10 of the second embodiment has the advantage described below.

(5) The correction unit 42 corrects the basic absorbance of the light received by the light receiver 24 based on the reference absorbance and the food color information. Thus, since the basic absorbance of the food differs in accordance with the color of the food M, the calorie measurement device 10 limits changes in the calculated calories. This allows the calorie measurement device 10 to further increase the measurement accuracy of the food calories.

Third Embodiment

The calorie measurement device 10 of a third embodiment differs from the calorie measurement device 10 of the first embodiment in the following points. In the third embodiment, like or same reference numerals are given to those components that are the same as the corresponding components of the first embodiment. Such components will not be described in detail.

The correction unit 42 of the first embodiment reduces changes in the basic absorbance of light received by the light receiver 24 that are caused by the influence of the influential factors. The correction unit 42 of the third embodiment reduces changes in the basic absorbance of the light received by the light receiver 24 that are caused by the influence of the influential factors and changes in the wavelength of the peak in the basic absorbance of light received by the light receiver 24 that are caused by the influence of environmental factors.

The environmental factors affect and change the wavelength of the peak in the absorbance of light of the infrared light region received by the light receiver 24 when measuring the calories of the food M. Examples of the environmental factors include temperature and humidity.

The correction of changes in the wavelength of the absorbance peak that are caused by differences in temperature serving as the environmental factor during measurement will now be described with reference to FIG. 9.

Figure 9A:
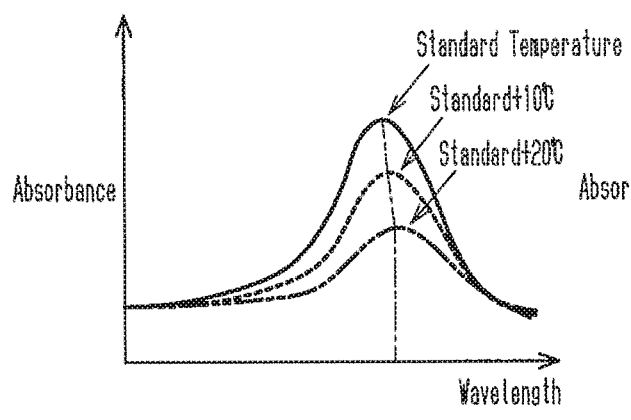
FIG. 9A is a graph showing the wavelength and the absorbance prior to correction in a third embodiment.

FIG. 9A shows spectrums of the basic absorbances of the amount of received light when the light, receiver 24 receives reflected light of the same food M under different temperature environments. The solid line in FIG. 9A shows the basic absorbance measured with a standard temperature. The standard temperature is used when measuring a large variety of calorie-known sample foods in the standard temperature to obtain the regression equation. The dotted line in FIG. 9A shows the basic absorbance measured at a temperature that is higher than the standard temperature by 10° C. The broken line in FIG. 9A shows the basic absorbance measured at a temperature that is higher than the standard temperature by 20° C.

The size and the peak wavelength are changed in accordance with the temperature during measurement in the basic absorbance of the light received by the light receiver 24.

The operation of the calorie measurement device 10 for limiting changes in the calorie measured in accordance with the temperature during measurement will now be described.

The measurement unit 20 includes a temperature detector (not shown), which is arranged in the measurement unit housing 21. The temperature detector detects the temperature of the inner side of the measurement unit housing 21 and outputs, to the analyzer 30, a measurement environment signal that changes in accordance with the temperature serving as a measurement temperature condition.

The calorie measurement device 10 measures many food samples in advance to obtain peak correction information in which measurement temperature dependency of the peak of the basic absorbance of light received by the light receiver 24 is statistically calculated. The calorie measurement device 10 stores, in the memory 43, the peak correction information in accordance with the temperature during measurement.

Figure 9B:
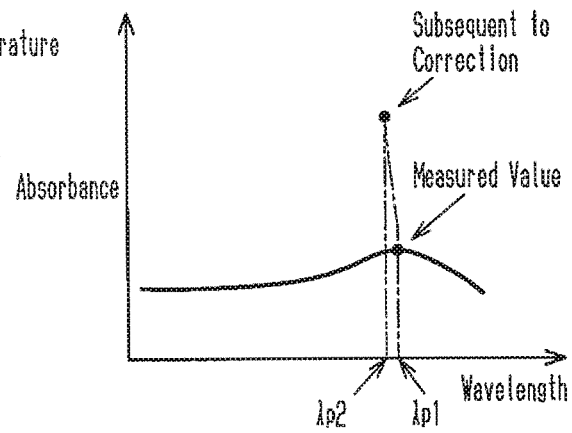
FIG. 9B is a graph showing the wavelength and the absorbance subsequent to correction in the third embodiment.

As shown in FIG. 9B, the correction unit 42 corrects the basic absorbance measured at a temperature higher than the standard temperature by 20° C. based on the measurement environment signal output by the temperature detector and the peak correction information stored in the memory 43 so that the corrected basic absorbance approaches the basic absorbance (reference absorbance) measured at the standard temperature. That is, the reference absorbance corresponding to the influential factors includes the basic absorbance of the standard temperature or a standard humidity. The correction unit 42 calculates the amount of correction from the difference of the calculated basic absorbance and the basic absorbance of the standard temperature or the standard humidity. More specifically, the correction unit 42 corrects the size and the peak wavelength of the basic absorbance having a first peak wavelength $\lambda 1$ at a temperature higher than the standard temperature by 20° C. to approach the basic absorbance having a second peak wavelength $\lambda 2$ at the standard temperature.

The calorie measurement device 10 may perform the same operation using the discrete value of a wavelength of the basic absorbance instead of the correction of the basic absorbance with consecutive spectrums of the basic absorbance of the light received by the light receiver 24 of FIG. 9.

In addition to advantages (1) to (4) of the calorie measurement device 10 of the first embodiment, the calorie measurement device 10 of the third embodiment has the advantage described below.

(6) The correction unit 42 corrects the size and peak wavelength of the basic absorbance of light received, by the light receiver 24 based on the influence of the environmental factors when the calories of the food M is measured. Thus, the calorie measurement device 10 limits changes in the calculated calories that are caused when the wavelength of the peak of the basic absorbance changes in accordance with the environmental factors during measurement. This allows the calorie measurement device 10 to further increase the measurement accuracy of the food calories.

Other Embodiments

The present calorie measurement device includes embodiments other than the first to third embodiments. Modified examples of the first to third embodiments serving as further embodiments of the present calorie measurement device will now be described. The modified examples may be combined with each other as long as technical contradictions do not occur.

The correction unit of a modified example corrects the amount of light received by the light receiver 24 based on the difference of the reference absorbance and the basic absorbance of the wavelength of a wavelength region having an extremely small contribution coefficient to the calories of the food M. The analysis unit 41 calculates the calories by applying the absorbance of the corrected light reception amount to the regression equation.

The light receiver of a modified example receives transmitted light in which the light emitted from the light emitter 22 is transmitted through the food M and outputs, to the correction unit 42, a light reception amount signal that changes in accordance with the amount of received light.

The correction unit of a modified example corrects at least one of the amount of light received by the light receiver 24 and the absorbance of light received by the light receiver 24 so that the calories calculated by the calorie measurement device 10 do not exceed the maximum value and the minimum value that are theoretically calculated.

The correction unit obtains the maximum value of the calories based on the weight of the food M that excludes water.

The light receiver of a modified example includes a spectrometer that performs spectral dispersion. This allows the calorie measurement device 10 to obtain the absorbance of light received by the light receiver 24 within a short time.

The analyzer 30 of a modified example includes a versatile computation processor such as a microcontroller. The analyzer 30 configures the analysis unit 41, the correction unit 42, and the controller 44 as a software function block of the versatile computation processor.

CLAUSES

This disclosure encompasses the following embodiments.

A calorie measurement device that analyzes a food for calories, the calorie measurement device including:
a light emitter that irradiates the food with light having a near-infrared wavelength;
a light receiver that receives at least one of transmitted light that has been transmitted through the food and reflected light that has been reflected by the food;
a correction unit that calculates a basic absorbance of the food based on at least one of the transmitted light and the reflected light and corrects at least one of the calculated basic absorbance and a light reception amount received by the light receiver based on an influential factor, wherein the influential factor affects absorption and reflection of light by a food and is not substantially affected by characteristics of the absorption and the reflection of the light of a food component; and
an analyzer that calculates an analyzed value indicating the calorie of the food based on at least one of the corrected basic absorbance and the corrected light reception amount received by the light receiver.

The calorie measurement device according to clause 1, further including a memory that stores a reference absorbance corresponding to the influential factor, wherein the correction unit reads the reference absorbance from the memory, calculates a correction amount from a difference of the calculated basic absorbance and the read reference absorbance, and corrects at least one of the basic absorbance and the light reception amount received by the light receiver in accordance with the calculated correction amount.

The calorie measurement device according to clause 2, wherein
the reference absorbance corresponding to the influential factor includes a reference absorbance of a predetermined wavelength range of the transmitted light or the reflected light that is not substantially affected by the characteristics of the absorption and the reflection of the light of the food component, and
the correction unit calculates the correction amount from a difference of the calculated basic absorbance in the predetermined wavelength range of the transmitted light or the reflected light and the read reference absorbance.

The calorie measurement device according to clause 3, wherein the food component includes at least one of protein, fat, and carbohydrate.

The calorie measurement device according to clause 3, wherein
the predetermined wavelength range is one of wavelength ranges,
the reference absorbance corresponding to the influential factor includes reference absorbances corresponding to wavelength ranges, and
the correction unit calculates correction amounts from a difference of the calculated basic absorbance in the wavelength ranges and the read reference absorbance and corrects at least one of the basic absorbance and the light reception amount received by the light receiver based on the calculated correction amounts.

The calorie measurement device according to clause 5, wherein the correction amount calculates a correction amount of an entire wavelength range by linearly or curvilinearly approximating the correction amounts and corrects at least one of the calculated basic absorbance and the light reception amount received by the light receiver in accordance with the correction amount of the entire wavelength range.

The calorie measurement device according to any one of clauses 1 to 6, wherein
the reference absorbance corresponding to the influential factor includes a basic absorbance of a food having a reference color, and
the correction unit calculates a correction amount from a difference of the calculated basic absorbance and the basic absorbance of the food having the reference color.

The calorie measurement device according to clause 7, wherein the reference color includes white.

The calorie measurement device according to any one of clauses 1 to 8, wherein
the reference absorbance corresponding to the influential factor includes a basic absorbance of a standard temperature or a standard humidity, and
the correction unit calculates a correction amount from a difference of the calculated basic absorbance and a basic absorbance of the standard temperature or the standard humidity.

The invention claimed is:

1. A calorie measurement device that analyzes a food for calories, the calorie measurement device comprising:
a light emitter that irradiates the food with light having a near-infrared wavelength;
a light receiver that receives at least one of transmitted light that has been transmitted through the food and reflected light that has been reflected by the food;
a memory that stores instructions and a regression equation for estimating calories of the food using an absorbance of each wavelength of the light received by the light receiver and a contribution coefficient of the absorbance of each wavelength, wherein the calories of the food serve as dependent variables, and each of the absorbance and contribution coefficient serve as an independent variable;
one or more processors that are connected to the memory and are configured when executing the instructions to:
calculate a basic absorbance of the food based on at least one of the transmitted light and the reflected light;
compare the basic absorbance with a reference absorbance used for defining the regression equation and specify a degree of influence an influential factor has on an absorption and a reflection of the light in the food based on the comparison result, wherein the influential factor affects absorption and reflection of light by a food and is not substantially affected by characteristics of the absorption and the reflection of the light of a food component, and the basic absorbance has a wavelength range that corresponds to the contribution coefficient having a smaller absolute value than other wavelength ranges and is not substantially affected by the characteristics of the absorption and the reflection of the light of a food component; and correct at least one of the calculated basic absorbance and a light reception amount received by the light receiver based on the specified degree of influence; and an analyzer that calculates an analyzed value indicating calories of a food by applying the corrected basic absorbance to the regression equation.

2. The calorie measurement device according to claim 1, wherein the one or more processors are further configured when executing the instructions to correct at least one of the calculated basic absorbance and the light reception amount received by the receiver based on the influential factor that reflects a light path in a food.

3. The calorie measurement device according to claim 1, wherein the one or more processors are further configured when executing the instructions to correct at least one of the calculated basic absorbance and the light reception amount received by the receiver based on the influential factor that reflects at least one of a reflectance and a transmittance of a food.

4. The calorie measurement device according to claim 1, wherein the one or more processors are further configured when executing the instructions to correct at least one of the calculated basic absorbance and the light reception amount received by the receiver based on an environmental factor that is the influential factor that affects a wavelength of a peak of the absorbance of a food.

5. The calorie measurement device according to claim 1, wherein the one or more processors are further configured when executing the instructions to correct at least one of the calculated basic absorbance and the light reception amount received by the receiver based on a color of a food that is the influential factor.

* * * * *